United States Patent
Noda et al.

(10) Patent No.: US 7,261,464 B2
(45) Date of Patent: Aug. 28, 2007

(54) C-ARM HOLDING APPARATUS AND X-RAY DIAGNOSTIC APPARATUS

(75) Inventors: Koji Noda, Nasushiobara (JP); Atsushi Gotoh, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/341,660

(22) Filed: Jan. 30, 2006

(65) Prior Publication Data
US 2006/0171508 A1 Aug. 3, 2006

(30) Foreign Application Priority Data
Jan. 31, 2005 (JP) .............................. 2005-024572

(51) Int. Cl.
*H05G 1/02* (2006.01)
(52) U.S. Cl. ...................................... 378/197; 378/195
(58) Field of Classification Search ........ 378/195–198, 378/193
See application file for complete search history.

(56) References Cited

U.S. PATENT DOCUMENTS

| | | | | |
|---|---|---|---|---|
| 4,922,512 A | * | 5/1990 | Lajus et al. ................. | 378/197 |
| 4,987,585 A | | 1/1991 | Kidd et al. | |
| 5,479,470 A | * | 12/1995 | Stenfors ...................... | 378/196 |
| 6,264,364 B1 | | 7/2001 | Pflaum et al. | |
| 6,309,102 B1 | | 10/2001 | Stenfors | |
| 6,315,446 B1 | * | 11/2001 | Kidd et al. .................. | 378/197 |
| 6,382,833 B2 | * | 5/2002 | Leandersson et al. ....... | 378/197 |
| 6,742,929 B2 | * | 6/2004 | Horbaschek ................ | 378/197 |
| 2002/0006185 A1 | * | 1/2002 | Lienard et al. ............. | 378/205 |
| 2004/0081285 A1 | * | 4/2004 | Gotoh ......................... | 378/193 |
| 2004/0170255 A1 | * | 9/2004 | Akutsu et al. .............. | 378/197 |

FOREIGN PATENT DOCUMENTS

| | | |
|---|---|---|
| EP | 0 224 886 A1 | 6/1987 |
| JP | 8-71062 | 3/1996 |
| JP | 2000-342639 | 12/2000 |
| JP | 2003-250784 | 9/2003 |
| JP | 2004-135777 | 5/2004 |

* cited by examiner

*Primary Examiner*—Hoon Song
(74) *Attorney, Agent, or Firm*—Oblon, Spivak, McClelland, Maier & Neustadt, P.C.

(57) ABSTRACT

An X-ray diagnostic apparatus includes a floor rotating arm which is installed at one end on a floor surface so as to be rotatable around a first rotation axis, a C-arm which is mounted on the other end of the floor rotating arm so as to be rotatable around a second rotation axis, an X-ray tube which is mounted on one end of the C-arm, an X-ray detector which is mounted on the other end of the C-arm, and a bed which has a table top provided to be movable along a longitudinal axis. The bed is placed such that the longitudinal axis is spaced apart from the first rotation axis by a predetermined distance.

9 Claims, 10 Drawing Sheets

C-ARM HOLDING APPARATUS AND X-RAY DIAGNOSTIC APPARATUS

CROSS-REFERENCE TO RELATED APPLICATIONS

This application is based upon and claims the benefit of priority from prior Japanese Patent Application No. 2005-024572, filed Jan. 31, 2005, the entire contents of which are incorporated herein by reference.

BACKGROUND OF THE INVENTION

1. Field of the Invention

The present invention relates to a C-arm holding apparatus and an X-ray diagnostic apparatus and, more particularly, to a floor type C-arm holding apparatus which holds an X-ray generating unit and an X-ray detecting unit so as to make them face each other, and an X-ray diagnostic apparatus having the C-arm holding apparatus.

2. Description of the Related Art

Medical imaging diagnostic techniques using X-ray diagnostic apparatuses, MRI apparatuses, and X-ray CT apparatuses have rapidly advanced with improvements in computer technology, and have become indispensable to current medical practice.

Recently, X-ray diagnosis has advanced mainly in the field of circulatory organs with improvements in catheter techniques. An X-ray diagnostic apparatus for the diagnosis of circulatory organs generally comprises an X-ray generating unit, an X-ray detecting unit, a holding apparatus which holds the X-ray generating unit and the X-ray detecting unit, a table top, a signal processing unit, a display unit, and the like. The holding apparatus allows X-ray imaging at an optimal position or in an optimal direction by pivoting, rotating, or moving a C-arm or Ceiling-traveling C or Ceiling-mounted arm around a patient (to be referred to as a subject hereinafter).

As a detector used for the X-ray detecting unit of an X-ray diagnostic apparatus, an X-ray film or an I.I. (Image Intensifier) has been used. In an X-ray imaging method using this I.I., X-ray projection data (to be referred to as projection data hereinafter) obtained when X-rays generated by the X-ray generating unit are transmitted through a subject is converted into an optical image by the I.I., and this optical image is displayed on a monitor after being converted into an electrical signal by an X-ray TV camera and digitized. Therefore, the X-ray imaging method using the I.I. allows real-time imaging which is impossible in the film system, and can acquire projection data in the form of digital signals. This makes it possible to perform various kinds of image processing. As a substitute for the above I.I., a flat panel detector comprising a two-dimensional array of detection elements has recently attracted attention. Some of such detectors have already been put into practical use.

FIG. 8 shows a C-arm holding apparatus used for a conventional circulatory organ X-ray diagnostic apparatus. An X-ray generating unit 101 is mounted on one end (lower end) of a C-arm 103 of a C-arm holding apparatus 105, and an X-ray detecting unit 102 comprising, for example, a flat panel detector is mounted on the other end (upper end) of the C-arm 103 so as to face the X-ray generating unit 101. A one-dot dashed line 108 in FIG. 8 represents an imaging central axis (isocenter) which connects the focal point of an X-ray tube in the X-ray generating unit 101 to the center of the flat panel detector of the X-ray detecting unit 102.

The C-arm 103 is held on a stand 105, fixed on a floor surface 106, through an arm holder 104. The C-arm 103 is mounted on an end portion of the arm holder 104 so as to be slidable in the direction indicated by an arrow a. The arm holder 104 is mounted on the upper portion of the stand 105 so as to be pivotal or rotatable in the direction indicated by an arrow b. The stand 105 comprises a stand fixed portion 105a fixed on the floor surface 106 and a stand movable portion 105b which can pivot about the column axis in the direction indicated by an arrow c.

The X-ray generating unit 101 and X-ray detecting unit 102 (to be collectively referred to as an imaging system hereinafter) are set at an optimal position in an optimal direction with respect to a subject (not shown) placed on a table top 107 by sliding the C-arm 103 in the direction a and pivoting the arm holder 104 in the direction b. In addition, the imaging system and the C-arm 103 can be retracted from the subject by pivoting the stand movable portion 105b in the direction c. Retracting the imaging system and the C-arm 103 makes it possible to ensure a working space around the head of the subject for a doctor or an examiner (to be referred to as an operator hereinafter) and facilitate replacement or repositioning of the subject on the table top 107 before or after examination, placement of anesthesia equipment, and the like.

Note that as the arm holder 104 described above, an L-shaped offset arm is generally used as shown in FIG. 8. Making the arm holder 104 have an L shape allows the C-arm 103 to be placed on a side of the table top 107. This makes it possible to move an end portion of the table top 107 in the longitudinal direction to near the stand 105 in the direction indicated by an arrow d. That is, using the L-shaped arm holder 104 makes it possible to enlarge the moving range of the table top 107 and expand the imaging range with respect to the subject. In addition, the L shape of the arm holder 104 have an advantage of being able to ensure a working space around the head of a subject for an operator.

However, the ensurance of a working space or the enlargement of the imaging range by pivoting the stand movable portion 105b or using the L-shaped arm holder 104 has its own limit because the stand 105 is fixed on the floor surface 106, and hence is not necessarily sufficient for the operator.

In order to solve such problems, a method has been proposed in which a ceiling-mounted C-arm holding apparatus having an arm whose one end is pivotally mounted on the ceiling and an arm holder mounted on the other end of the arm is used, and an imaging region of a subject can be arbitrarily set by aligning the position of the pivot axis of the arm with the central line of a table top in the longitudinal direction (see Jpn. Pat. Appln. KOKAI Publication No. 2000-70248).

According to the method disclosed in the above reference, since the arm holder is held on the ceiling through the arm, this holding apparatus has no stand fixed on the floor surface, unlike the conventional floor type C-arm holding apparatus shown in FIG. 8. Therefore, there is no obstacle to the movement of the table top, and the imaging system can be set at an optimal position with respect to any imaging target region of a subject.

However, the C-arm holding apparatus of a circulatory organ X-ray diagnostic apparatus is basically a floor type apparatus. It is therefore necessary for this floor type C-arm holding apparatus to ensure a sufficient work space and allow easy X-ray imaging at an arbitrary position without any limitation on the imaging range. In a dual plane system having an imaging system for cardiac angio, which is used for X-ray imaging with a relatively narrow field of view, and an imaging system for general angio, which is used for X-ray imaging with a wide field of view, e.g., imaging of the head or the lower limbs, two C-arm holding apparatuses, i.e., a floor type apparatus and a ceiling-traveling type apparatus, must be selectively used. When, in particular, the ceiling-traveling C-arm holding apparatus is to be used, it is desired that the floor type C-arm holding apparatus be retracted to an optimal area.

BRIEF SUMMARY OF THE INVENTION

It is an object of the present invention to provide a floor type C-arm holding apparatus with a high degree of freedom in operation, and an X-ray diagnostic apparatus.

According to an aspect of the present invention, there is provided an X-ray diagnostic apparatus comprising a floor rotating arm which is installed at one end on a floor surface so as to be rotatable around a first rotation axis, a C-arm which is mounted on the other end of the floor rotating arm so as to be rotatable around a second rotation axis, an X-ray tube which is mounted on one end of the C-arm, an X-ray detector which is mounted on the other end of the C-arm, and a bed which has a table top provided to be movable along a longitudinal axis, the bed being placed such that the longitudinal axis is spaced apart from the first rotation axis by a predetermined distance.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

In the embodiment of the present invention which will be described below, the stand of a C-arm holding apparatus is pivotally mounted on one end of a floor rotating arm having the other end pivotally mounted on the floor surface, and a C-arm having an imaging system (an X-ray generating unit and an X-ray detecting unit) mounted on its end portion is mounted on the stand through an arm holder. The stand and the C-arm and imaging system mounted on the stand are moved to predetermined positions in predetermined directions by pivoting the floor rotating arm and the stand.

(Arrangement of Apparatus)

Figure 1:
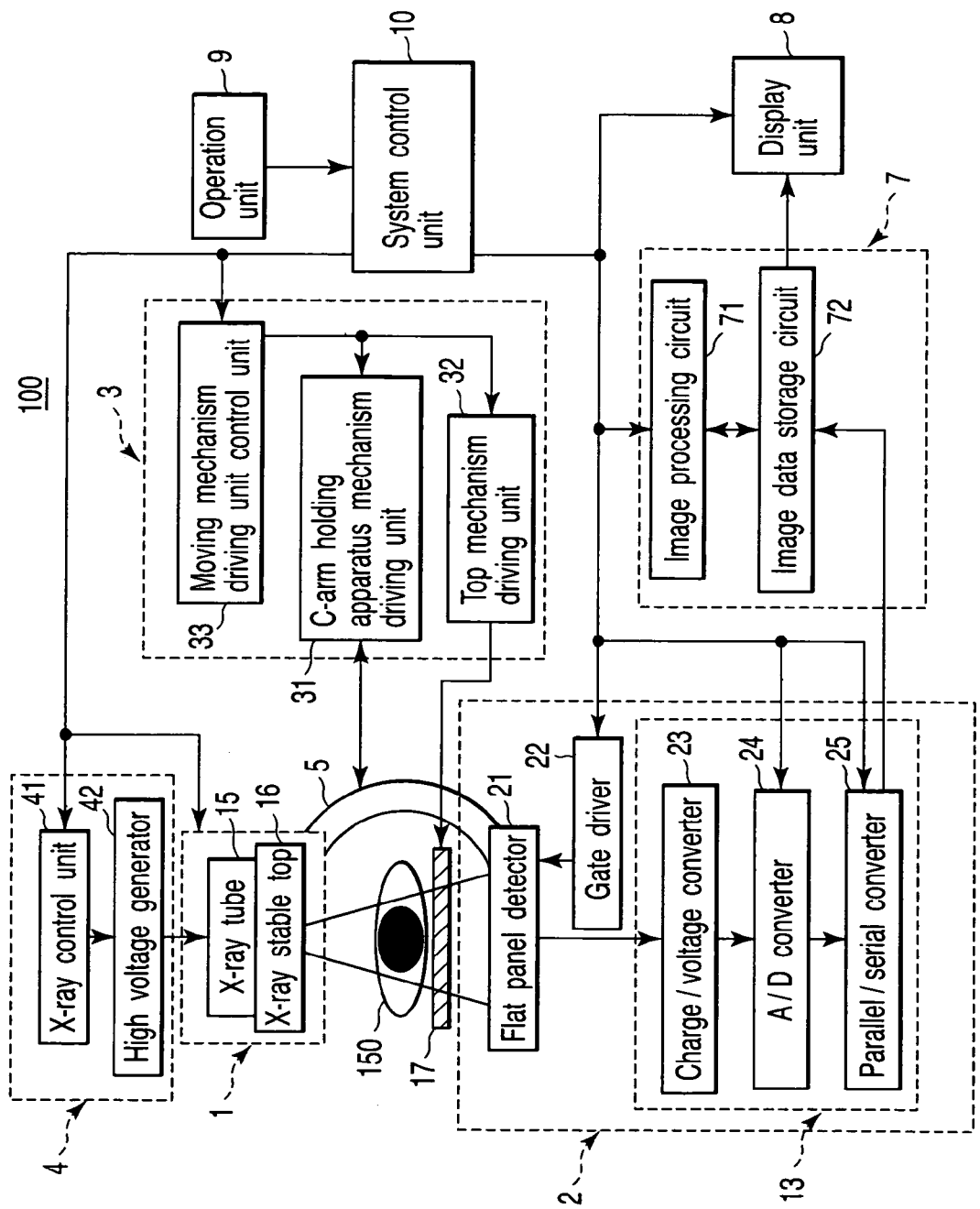
FIG. 1 is a block diagram showing the overall arrangement of an X-ray diagnostic apparatus according to an embodiment of the present invention.
Figure 2:
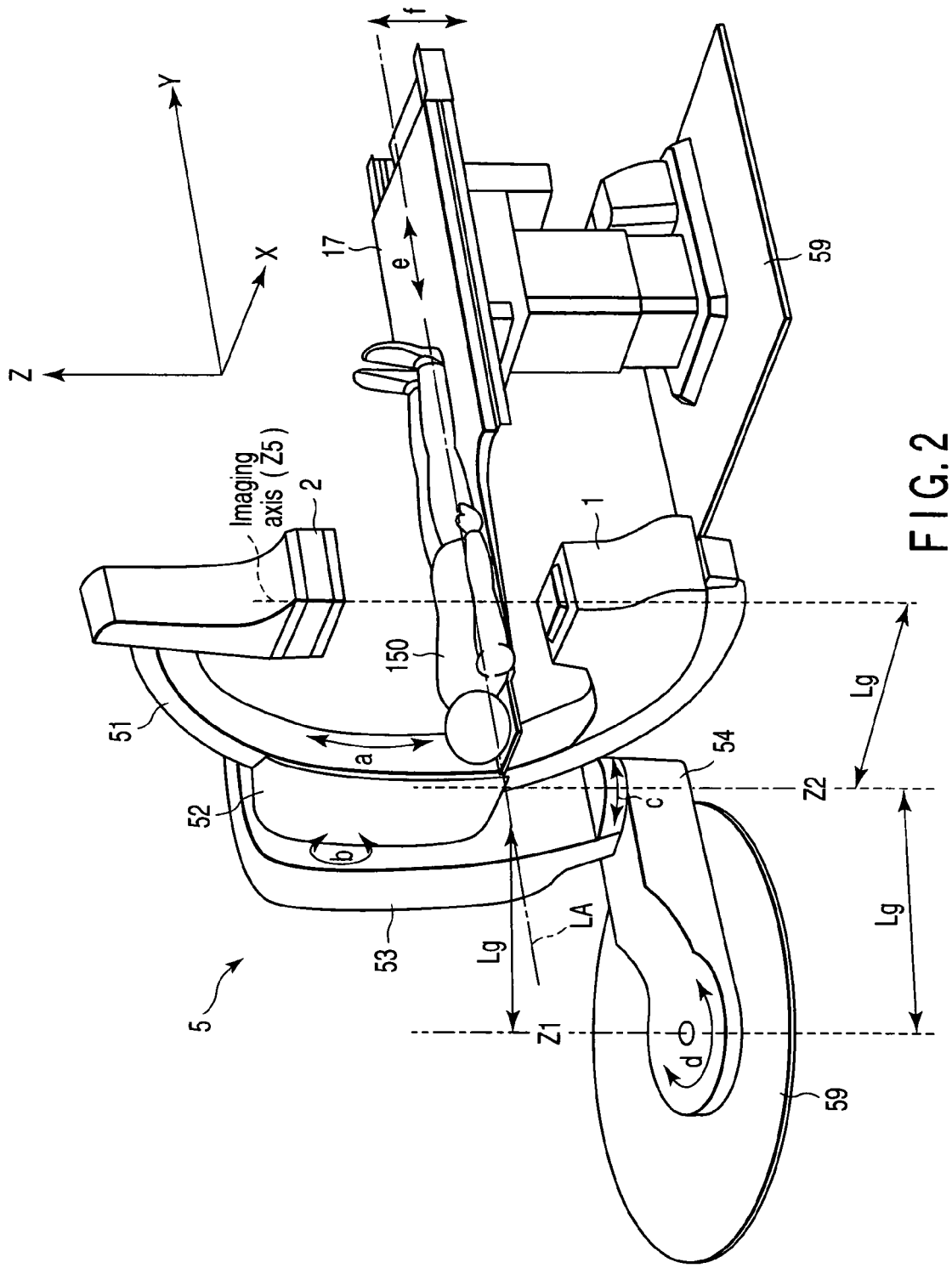
FIG. 2 is a view showing the arrangement of a C-arm holding apparatus according to the embodiment.

The arrangement of an X-ray diagnostic apparatus according to an embodiment of the present invention will be described with reference to FIGS. 1 to 3. FIG. 1 is a block diagram showing the overall arrangement of the X-ray diagnostic apparatus. FIG. 2 is a view showing the arrangement of the C-arm holding apparatus.

An X-ray diagnostic apparatus 100 comprises an X-ray generating unit 1 which applies X-rays to a subject 150, an X-ray detecting unit 2 which two-dimensionally detects X-rays transmitted through the subject 150 and generates X-ray projection data on the basis of the X-ray detection data, a C-arm holding apparatus 5 which holds the X-ray generating unit 1 and the X-ray detecting unit 2, a table top 17 on which the subject 150 is to be placed, and a high voltage generating unit 4 which generates a high voltage necessary for X-ray application by the X-ray generating unit 1.

The X-ray diagnostic apparatus 100 comprises a moving mechanism driving unit 3 which supplies driving signals to a sliding mechanism, pivoting mechanism, and moving mechanism provided for the C-arm holding apparatus 5 and the table top 17, an image processing storage unit 7 which generates and stores image data on the basis of the X-ray projection data generated by the X-ray detecting unit 2, and a display unit 8 which displays desired image data of a plurality of frames of image data stored in the image processing storage unit 7.

The X-ray diagnostic apparatus 100 further has an operation unit 9 which is used to, for example, select and set subject information, imaging conditions, display conditions, X-ray application conditions, and the like and input various commands, and a system control unit 10 which systematically controls the above units of the X-ray diagnostic apparatus 100.

The X-ray generating unit 1 comprises an X-ray tube 15 which applies X-rays to the subject 150 and an X-ray stable top 16 which forms X-rays applied from the X-ray tube 15 into an X-ray cone (cone beam). The X-ray tube 15 is a vacuum tube which generates X-rays and generates X-rays by accelerating electrons emitted from a cathode (filament) using a high voltage and making the electrons collide with a tungsten anode. The X-ray stable top 16 is placed between the X-ray tube 15 and the subject 150 and has a function of reducing the size of an X-ray beam applied from the X-ray tube 15 into a predetermined irradiation size.

The X-ray detecting unit 2 comprises a flat panel detector 21 which converts X-rays transmitted through the subject 150 into charge and stores it, a gate driver 22 which reads out charge stored in the flat panel detector 21, and a projection data generating unit 13 which generates X-ray projection data from the read charge.

The flat panel detector 21 is formed by two-dimensionally arraying minute detection elements in the column and line directions. Each detection element comprises a photoelectric film which detects X-rays and generates charge in accordance with the amount of incident X-rays, a charge storage capacitor which stores charge generated in the photoelectric film, and a Thin-Film Transistor (TFT) which reads out charge stored in the charge storage capacitor at a predetermined timing.

The projection data generating unit 13 comprises a charge/voltage converter 23 which converts the charge read by the flat panel detector 21 into a voltage, an A/D converter 24 which converts an output from the charge/voltage converter 23 into a digital signal, and a parallel/serial converter 25 which converts X-ray projection data, which is parallelly read from the flat panel detector 21 on a line basis and digitally converted, into a time-series signal.

The moving mechanism driving unit 3 comprises a C-arm holding apparatus mechanism driving unit 31 which supplies driving signals to a sliding mechanism, pivoting mechanism, and moving mechanism provided for the C-arm holding apparatus 5 (to be described later), a table top mechanism driving unit 32 which supplies driving signals for the movement of the table top 17 in the vertical direction and along a longitudinal axis LA, and a moving mechanism driving unit control unit 33 which controls the C-arm holding apparatus mechanism driving unit 31 and the table top mechanism driving unit 32.

The arrangement of the C-arm holding apparatus 5 which is the most important portion of this embodiment will be described next with reference to FIG. 2. FIG. 2 shows the C-arm holding apparatus 5 on which the X-ray generating unit 1 and the X-ray detecting unit 2 are mounted and the table top 17 on which the subject 150 is placed. Referring to FIG. 2, for the sake of descriptive convenience, the body axis direction of the subject 150, i.e., the longitudinal axis LA of the table top 17, is set as the Y-axis, the central axis direction (pivot axis direction) of a stand 53 is set as the Z-axis, and the direction perpendicular to the Y-axis and the Z-axis is set as the X-axis. However, the body axis direction of the subject 150 can be set to an arbitrary direction with respect to the C-arm holding apparatus 5.

Figure 8:
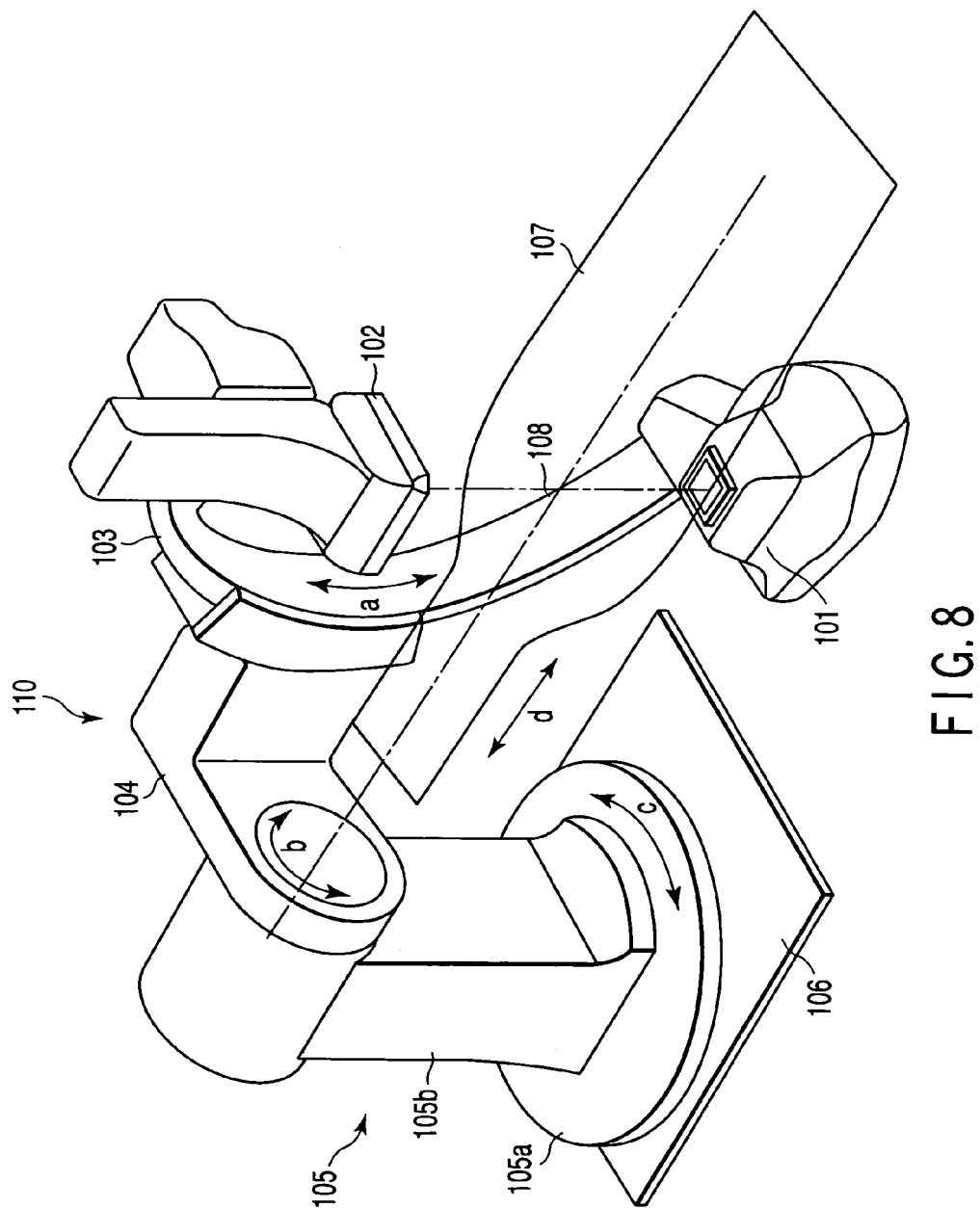
FIG. 8 is a perspective view showing a conventional floor type C-arm holding apparatus.

Like the conventional C-arm holding apparatus 110 shown in FIG. 8, the C-arm holding apparatus 5 is designed such that the X-ray generating unit 1 is mounted on one end (lower end) of a C-arm 51, and the X-ray detecting unit 2 is mounted on the other end (upper end) of the C-arm 51 so as to face the X-ray generating unit 1.

The C-arm 51 is held on the stand 53 through an arm holder 52. The C-arm 51 is mounted on a side surface of the arm holder 52 so as to be slidable in the direction indicated by an arrow a. The arm holder 52 is mounted on the stand 53 so as to be pivotal about a pivot axis in the direction indicated by an arrow b, i.e., the X direction. As the arm holder 52 pivots, the C-arm 51 pivots about the pivot axis in the X direction. By sliding the C-arm 51 in the direction a and pivoting the arm holder 52 in the direction b, the imaging system mounted on the two end portions of the C-arm 51 is set at an arbitrary position with respect to the subject 150 placed on the table top 17.

A floor rotating arm 54 is placed on a floor surface 59. One end of the floor rotating arm 54 is mounted on the floor surface 59 so as to be pivotal about a rotation axis Z1 (first pivot axis), and the stand 53 is mounted on the other end of the floor rotating arm 54 so as to be pivotal about a rotation axis Z2 (second pivot axis). In this case, both the rotation axis Z1 of the floor rotating arm 54 and the rotation axis Z2 of the stand 53 are set to be located in the Z direction. Pivoting the floor rotating arm 54 about the rotation axis Z1 makes it possible to retract the stand 53, arm holder 52, and C-arm 51 to positions distant from the subject 150.

In addition, combining the pivotal movement of the floor rotating arm 54 and the pivotal movement of the stand 53 about the rotation axis Z2 on the floor rotating arm 54 makes it possible to set the imaging system at an arbitrary position in an arbitrary direction with respect to the subject 150 without interference from the stand 53. This allows X-ray imaging in a wide range from the head to the lower limbs and facilitates "head-first placement" and "lateral placement" of the imaging system with respect to the subject 150. The effects of this embodiment with respect to "head-first placement" and "lateral placement" of the imaging system will be described in detail later.

A C-arm sliding mechanism 511 for sliding the C-arm 51 is provided at the joint portion between the arm holder 52 and the C-arm 51. An arm holder pivoting mechanism 512 for pivoting the arm holder 52 is provided at the joint portion between the stand 53 and the arm holder 52. In addition, a stand pivoting mechanism 513 for pivoting the stand 53 is provided at the joint portion between the floor rotating arm 54 and the stand 53. A floor rotating arm pivoting mechanism 514 for pivoting the floor rotating arm 54 is provided at the joint portion between the floor rotating arm 54 and the floor surface 59. These mechanisms are not shown in FIG. 2.

Figure 9A:
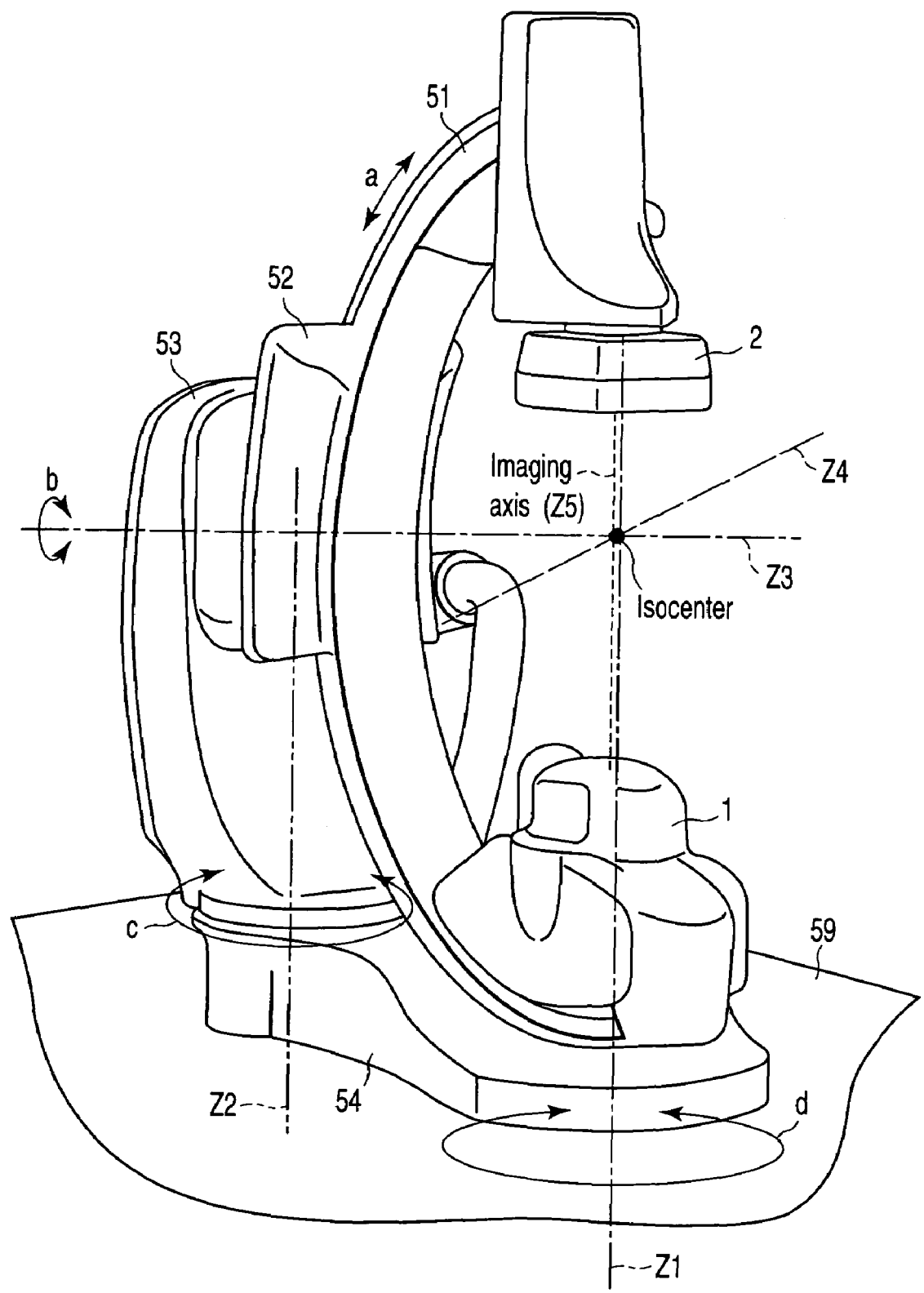
FIG. 9A is a perspective view of a C-arm holding apparatus in FIG. 2.
Figure 9:
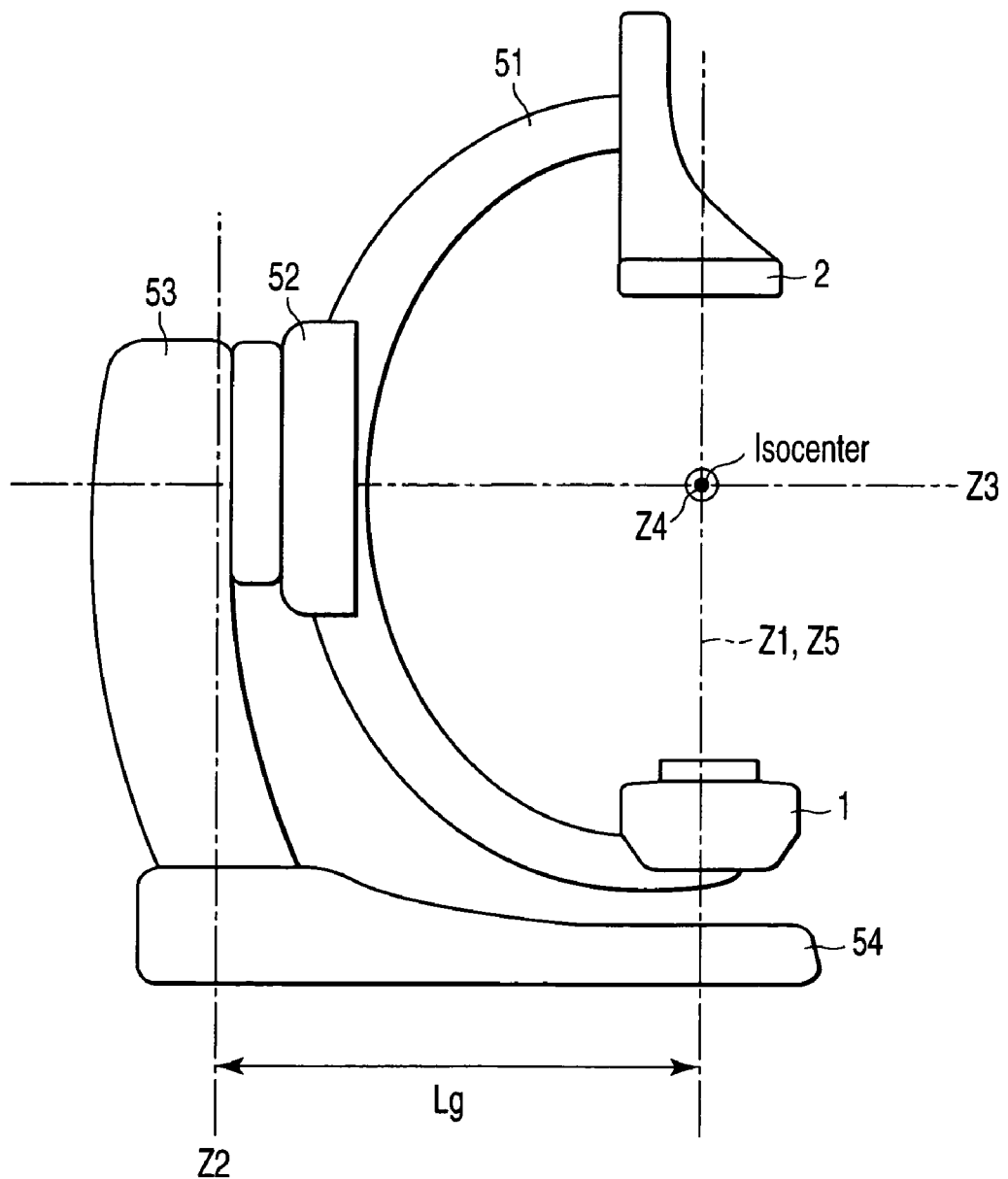
FIG. 9B is a side view of the C-arm holding apparatus in FIG. 2.

The C-arm holding apparatus 5 will be described in detail. As shown in FIGS. 9A and 9B, the floor rotating arm 54 is provided, at one end, on the floor surface so as to be rotatable (d) around the substantially vertical first rotation axis Z1. The stand 53 is supported on the other end of the floor rotating arm 54 so as to be rotatable (c) around the substantially vertical second rotation axis Z2. The arm holder 52 is supported on the stand 53 so as to be rotatable (B) around a substantially horizontal third rotation axis (C-arm horizontal rotation axis) Z3. The C-arm 51 is supported on the arm holder 52 so as to be slidable/rotatable around a substantially horizontal fourth rotation axis (slide rotation axis) Z4 perpendicular to the C-arm horizontal rotation axis Z3. The X-ray generating unit 1 is mounted on one end of the C-arm 51. The X-ray detecting unit 2 is mounted on the other end of the C-arm 51.

This apparatus is designed such that the X-ray focal point of the X-ray generating unit 1 and the imaging axis passing through the center of the detection surface of the X-ray detecting unit 2 cross the C-arm horizontal rotation axis Z3 and the slide rotation axis Z4 at one point. As is known, the absolute coordinates of the intersection (a position on the imaging room coordinate system) does not displace even when the C-arm 51 rotates around the C-arm horizontal rotation axis Z3 and rotates around the slide rotation axis Z4 as long as the floor rotating arm 54 does not rotate around the first rotation axis Z1, and the stand 53 does not rotate around the second rotation axis Z2, and is generally called an isocenter.

Figure 5:
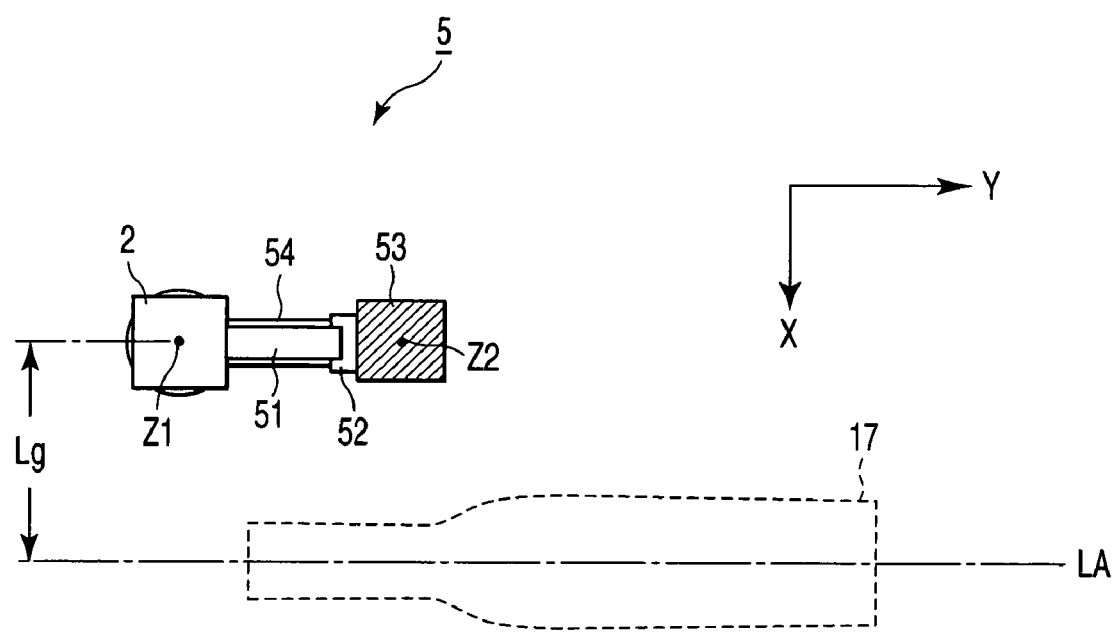
FIG. 5 is a view showing the retraction position of the C-arm holding apparatus in the embodiment.

As shown in FIGS. 9A, 9B, and 5, this apparatus is designed such that when the rotational angle of the stand 53 around the second rotation axis Z2 is set at a reference angle (0°) and the C-arm 51 overlaps the floor rotating arm 54 and is folded into the minimum posture, the isocenter is located at the first rotation axis Z1 of the floor rotating arm 54, that is, the imaging axis, the C-arm horizontal rotation axis Z3, and slide rotation axis Z4 cross the first rotation axis Z1 of the floor rotating arm 54 at the isocenter. That is, the length of the floor rotating arm 54, the size of the stand 53, the size of the arm holder 52, and the radius of the C-arm 51 are comprehensively determined such that the distance between the first rotation axis Z1 of the floor rotating arm 54 and the second rotation axis Z2 of the stand 53 becomes equal to the distance between the second rotation axis Z2 of the stand 53 and the isocenter.

Assume that the rotational angle of the C-arm 51 around the C-arm horizontal rotation axis Z3 is at the reference angle (0°), and the rotational angle of the C-arm 51 around the slide rotation axis Z4 is at the reference angle (0°) to set the imaging axis in the vertical direction. According to the above designs, in this case, when the rotational angle of the stand 53 around the second rotation axis Z2 is at the reference angle (0°), the imaging axis substantially coincides with the first rotation axis Z1 of the floor rotating arm 54.

Such structural characteristics act advantageously in various respects in imaging operation.

Figure 3:
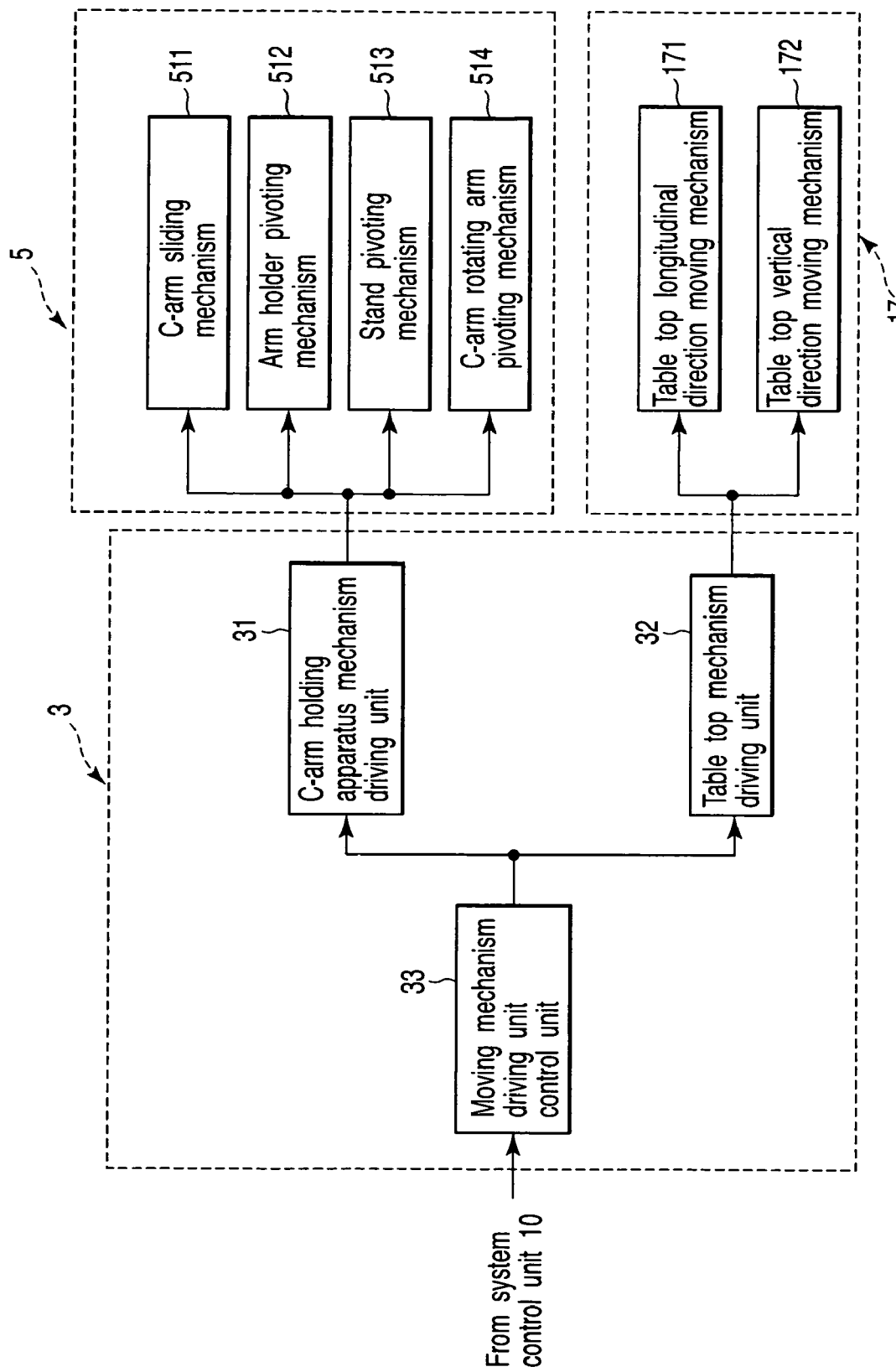
FIG. 3 is a block diagram showing a method of supplying driving signals to a sliding mechanism, pivoting mechanism, and moving mechanism provided for the C-arm holding apparatus and a table top in the embodiment.

As shown in FIG. 3, each mechanism described above slides or pivots to a desired position by a driving signal supplied from the C-arm holding apparatus mechanism driving unit 31 of the moving mechanism driving unit 3 on the basis of a control signal from the system control unit 10.

Referring to FIG. 2, the table top 17 on which the subject 150 is placed is provided with a table top longitudinal direction moving mechanism 171 (not shown) for moving the table top 17 in the body axis direction of the subject 150, i.e., the Y direction of the table top longitudinal axis LA, and a table top vertical direction moving mechanism 172 (not shown) for moving the table top 17 in the vertical direction (Z direction). Each of these moving mechanisms is moved to a desired position by a driving signal supplied from the table top mechanism driving unit 32 of the moving mechanism driving unit 3 on the basis of a control signal from the system control unit 10.

Referring back to FIG. 1, the high voltage generating unit 4 comprises a high voltage generator 42 which generates a high voltage to be applied between the anode and the cathode to accelerate thermal electrons generated from the cathode of the X-ray tube 15, and an X-ray control unit 41 which controls X-ray application conditions such as a tube current, tube voltage, and application time in the high voltage generator 42 in accordance with an instruction signal from the system control unit 10.

An image data storage circuit 72 of the image processing storage unit 7 generates image data by sequentially storing X-ray projection data output from the projection data generating unit 13 of the X-ray detecting unit 2 on a line basis. An image processing circuit 71 has an image processing function of, for example, generating DSA image data by performing differential processing with respect to image data generated by the image data storage circuit 72 on the basis of mask image data and contrast image data which are obtained in X-ray imaging before and after injection of a contrast medium.

The operation unit 9 is an interactive interface comprising input devices such as a keyboard, trackball, joy stick, and mouse, a display panel, various kinds of switches, and the like, and is used to, for example, input subject information, set X-ray application conditions and an image magnification, select the "imaging system placement mode" or "retraction mode", set an imaging system position and direction, and input various kinds of commands such as an imaging start command. Note that the X-ray application conditions include a tube voltage to be applied to the X-ray tube 15, a tube current, X-ray application time, and the like, and the subject information includes an age, sex, physique, examination region, examination method, diagnosis history, and the like. In addition, the "imaging system placement mode" includes a "head-first placement mode" and a "lateral placement mode".

The display unit 8 displays the image data generated by the image data storage circuit 72 of the image processing storage unit 7. The system control unit 10 comprises a CPU and storage circuit (not shown) temporarily stores pieces of information such as command signals and various kinds of initial setting conditions input by the operator, which are supplied from the operation unit 9, and then systematically controls the respective units of the X-ray diagnostic apparatus 100 on the basis of these pieces of information.

Figure 4A:
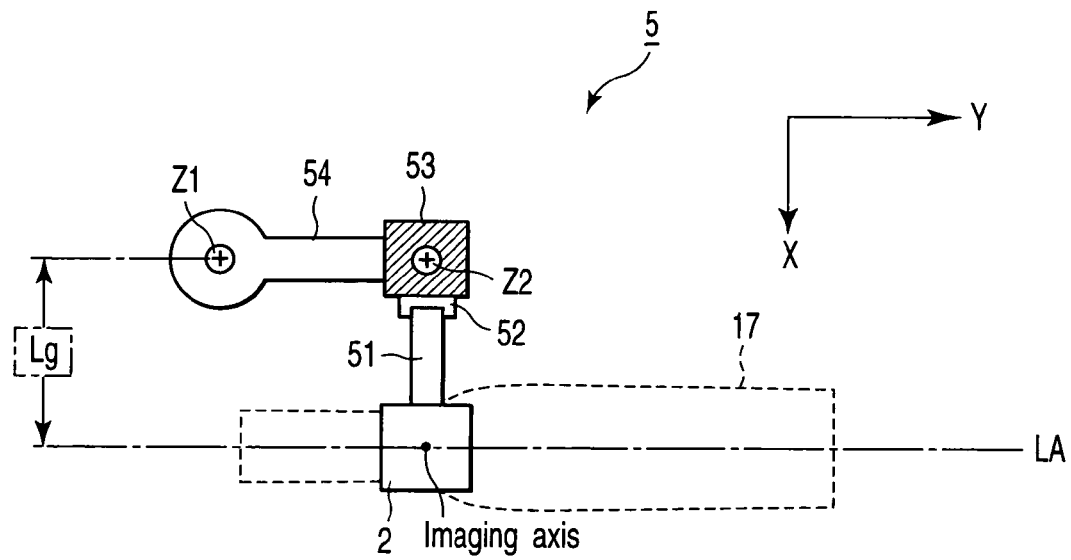
FIG. 4A is a view for explaining a "lateral placement mode" in the embodiment.

An example of installation of the C-arm holding apparatus 5 in this embodiment will be described next with reference to FIGS. 4A, 4B, and 5. FIG. 4A shows a so-called "lateral placement mode" in which the imaging system is placed from a side of the subject by using the C-arm holding apparatus 5. When a user instruction associated with the activation of the "lateral placement mode" is input through the operation unit 9, the moving mechanism driving unit control unit 33 realizes the placement shown in FIG. 4A by controlling the respective units in response to the user instruction. That is, the floor rotating arm 54 pivots about the rotation axis Z1 so as to be positioned substantially parallel to the longitudinal axis LA of the table top 17, and the stand 53 pivots about the rotation axis Z2 of the floor rotating arm 54 so as to make the C-arm 51 cross the longitudinal axis LA at a substantially right angle.

In performing X-ray imaging while moving the table top 17 in the longitudinal direction, placing the stand 53 on a side of the table top 17 makes it possible to perform X-ray imaging in a wide range from the head to the lower limbs because the moving range of the table top 17 is not restricted by the stand 53. Note, however, that a distance Lg is set between the rotation axis Z1 of the floor rotating arm 54 mounted on the floor surface 59 and the central axis of the table top 17 so as not to cause the table top 17 to come into contact with the stand 53 even if it moves in the longitudinal direction.

Figure 4B:
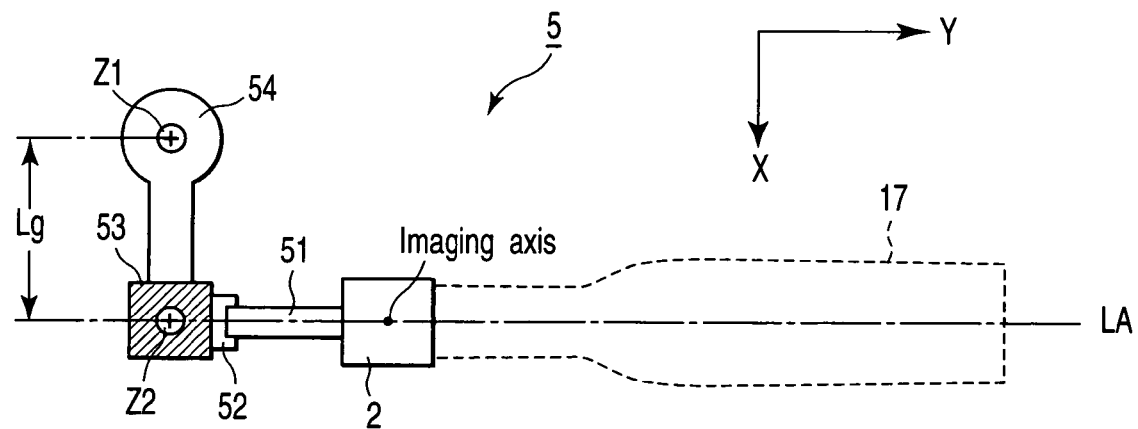
FIG. 4B is a view for explaining a "head-first placement mode" in the embodiment.

FIG. 4B shows a so-called "head-first placement mode" in which the imaging system is placed from the body axis direction of the head by using the C-arm holding apparatus 5. When a user instruction associated with the activation of the "head-first placement mode" is input through the operation unit 9, the moving mechanism driving unit control unit 33 realizes the placement shown in FIG. 4B by controlling the respective units in response to the user instruction. That is, the floor rotating arm 54 pivots about the rotation axis Z1 so as to be positioned substantially vertical to the longitudinal direction (Y direction) of the table top 17. The stand 53 placed on the other end of the floor rotating arm 54 then pivots about the rotation axis Z2 so as to make the C-arm 51 become substantially parallel to the longitudinal direction of the table top 17. In this case, the stand 53 is placed on the substantially central axis of the table top 17. By pivoting the floor rotating arm 54 about the rotation axis Z1, the stand 53 is placed on the substantially central axis of the table top 17. This makes it possible to perform the conventional "head-first placement mode".

FIG. 5 shows the retraction position of the C-arm holding apparatus 5 at the time of interruption or stable toppage of X-ray imaging. When a user instruction associated with the activation of the "retraction mode" is input through the operation unit 9, the moving mechanism driving unit control unit 33 realizes the placement shown in FIG. 5 by controlling the respective units in response to the user instruction. That is, the floor rotating arm 54 pivots about the rotation axis Z1 so as to be positioned substantially parallel to the longitudinal axis (Y direction) of the table top 17, and the stand 53 pivots about the rotation axis Z2 of the floor rotating arm 54 so as to make the C-arm 51 become parallel to the longitudinal direction of the table top 17. In this case, the above floor rotating arm 54 and stand 53 are pivoted such that the imaging central axis (isocenter) of the imaging system mounted on the C-arm 51 substantially coincides with the rotation axis Z1 of the floor rotating arm 54, and the C-arm 51 overlaps on the floor rotating arm 54.

The pivoting mechanisms in the C-arm holding apparatus 5 in this embodiment are realized by motor-driven operation. When the operator selects the "head-first placement mode" or "lateral placement mode" in selecting an "imaging system placement mode" using the operation unit 9, this selection information is supplied to the moving mechanism driving unit control unit 33 of the moving mechanism driving unit 3 through the system control unit 10. Upon receiving the selection information, the moving mechanism driving unit control unit 33 supplies a driving control signal to the C-arm holding apparatus mechanism driving unit 31. The C-arm holding apparatus mechanism driving unit 31 supplies, to the floor rotating arm pivoting mechanism 514 and stand pivoting mechanism 513 provided on the C-arm holding apparatus 5, a driving signal for pivoting the floor rotating arm 54 about the rotation axis Z1 and a driving signal for pivoting the stand 53 about the rotation axis Z2. By supplying these driving signals to the floor rotating arm pivoting mechanism 514 and the stand pivoting mechanism 513, "lateral placement" or "head-first placement" of the imaging system shown in FIG. 4A or 4B is performed.

In the same manner, when the "retraction mode" for retracting the C-arm holding apparatus 5 is selected by the operator using the operation unit 9 at the time of interruption or stable toppage of X-ray imaging, the C-arm holding apparatus mechanism driving unit 31 of the moving mechanism driving unit 3 supplies, on the basis of a selection signal from the operation unit 9, driving signals to the floor rotating arm pivoting mechanism 514 and the stand pivoting mechanism 513 by the same sequence as that for the "head-first placement mode" or "lateral placement mode" described above. The C-arm holding apparatus 5 shown in FIG. 5 is then retracted on the basis of these driving signals.

According to this embodiment described above, pivotally mounting the stand of the C-arm holding apparatus on one end of the floor rotating arm having the other end pivotally mounted on the floor surface makes it possible to place the stand outside the moving range of the table top. For this reason, even if the table top is moved in the longitudinal direction, it does not come into contact with the C-arm holding apparatus. This makes it possible to perform X-ray imaging with respect to the subject at an arbitrary position in an arbitrary direction without much restriction on the imaging range. In the "lateral placement mode", in particular, since no restriction is imposed on the moving range of the table top, X-ray imaging can be performed in a wide range from the head to the lower limbs.

In addition, since there is no need to install the stand of the C-arm holding apparatus around the subject placed on the table top, a sufficient working space can be ensured, and replacement or repositioning of the subject on the table top before or after examination, placement of anesthesia equipment, and the like are facilitated.

(Modification)

Figure 6:
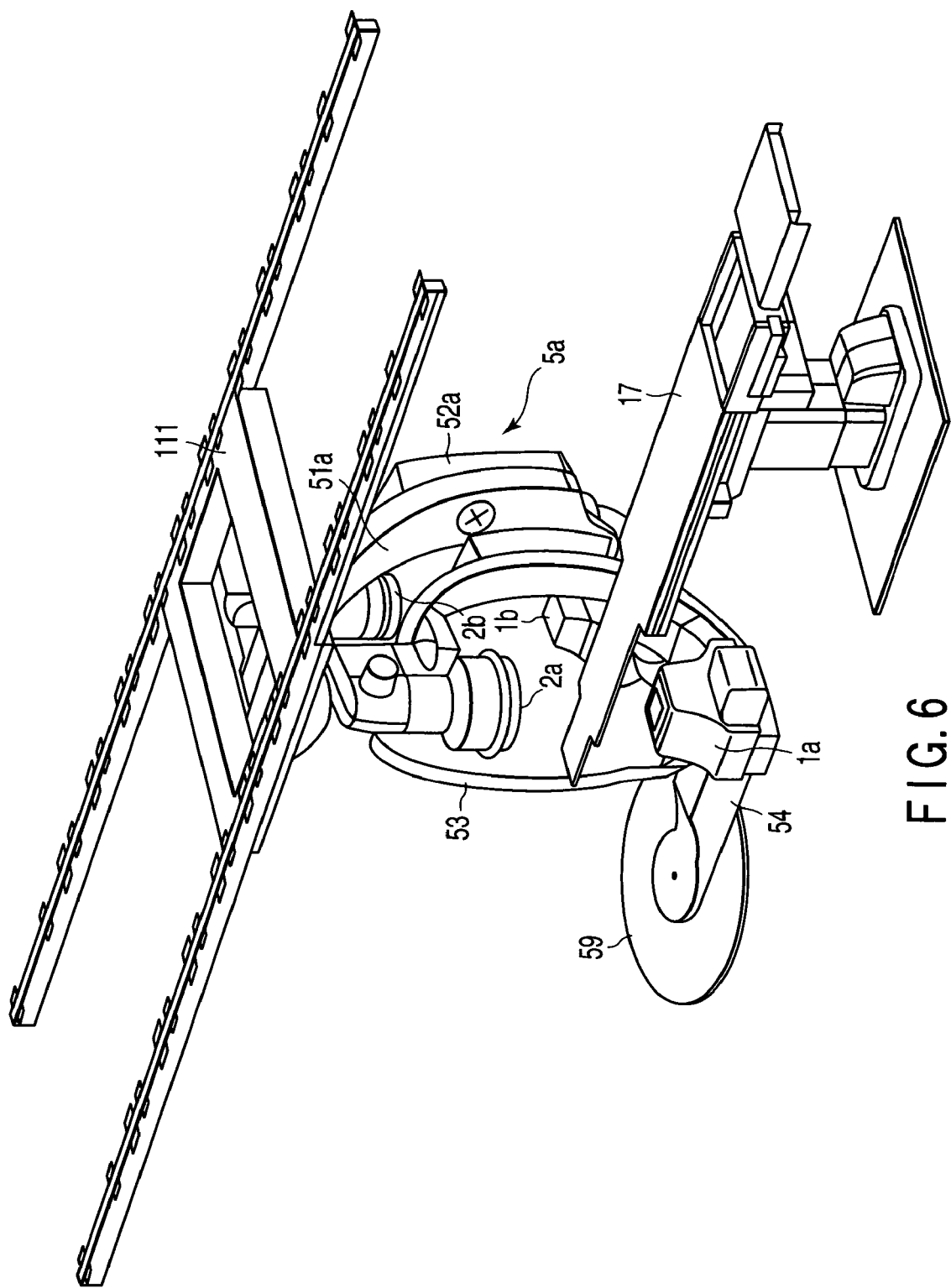
FIG. 6 is a perspective view showing a ceiling-traveling C-arm holding apparatus and a floor type C-arm holding apparatus according to a modification of the embodiment.

A modification of this embodiment will be described next with reference to FIGS. 6 to 8. The X-ray diagnostic apparatus according to this modification comprises a floor type C-arm holding apparatus like that in the above embodiment and a ceiling-traveling C-arm holding apparatus. That is, as shown in FIG. 6, this apparatus comprises a first imaging system having an X-ray generating unit 1a and an X-ray detecting unit 2a arranged on both sides of the subject (not shown) placed on the table top 17, and a second imaging system having an X-ray generating unit 1b and an X-ray detecting unit 2b. The X-ray generating unit 1a and the X-ray detecting unit 2a are mounted on a ceiling-traveling C-arm holding apparatus 5a, and the X-ray generating unit 1b and the X-ray detecting unit 2b are mounted on a floor type C-arm holding apparatus 5b having an arrangement similar to that in the above embodiment. In this case, the moving mechanism driving unit 3, image processing storage unit 7, display unit 8, operation unit 9, and system control unit 10 are shared between the above two C-arm holding apparatuses. The functions of these units are almost the same as those shown in FIG. 11, and hence a detailed description thereof will be omitted.

For the sake of descriptive convenience, FIG. 6 shows the case wherein the two imaging systems are arranged around the table top 17. In practice, however, the operator selects a desired imaging system and the C-arm holding apparatus on which the imaging system is mounted by using the operation unit 9, and the C-arm holding apparatus which is not selected is automatically retracted to a predetermined area.

That is, the X-ray diagnostic apparatus of this modification is a dual plane system having an imaging system for cardiac angio, which is used for X-ray imaging with a relatively narrow field of view, and an imaging system for general angio, which is used for X-ray imaging with a wide field of view, e.g., imaging of the head or the lower limbs. The imaging system for cardiac angio is mounted on the floor type C-arm holding apparatus 5b. The imaging system for general angio is mounted on the ceiling-traveling C-arm holding apparatus 5a. When X-ray imaging in the "head-first placement mode" is to be performed by using the ceiling-traveling C-arm holding apparatus 5a in this dual plane system, since the stand of the conventional floor type C-arm holding apparatus is fixed within the moving range of the table top, the stand comes into contact with the ceiling-traveling C-arm holding apparatus, resulting in difficulty in performing X-ray imaging in the "head-first placement mode".

Figure 7A:
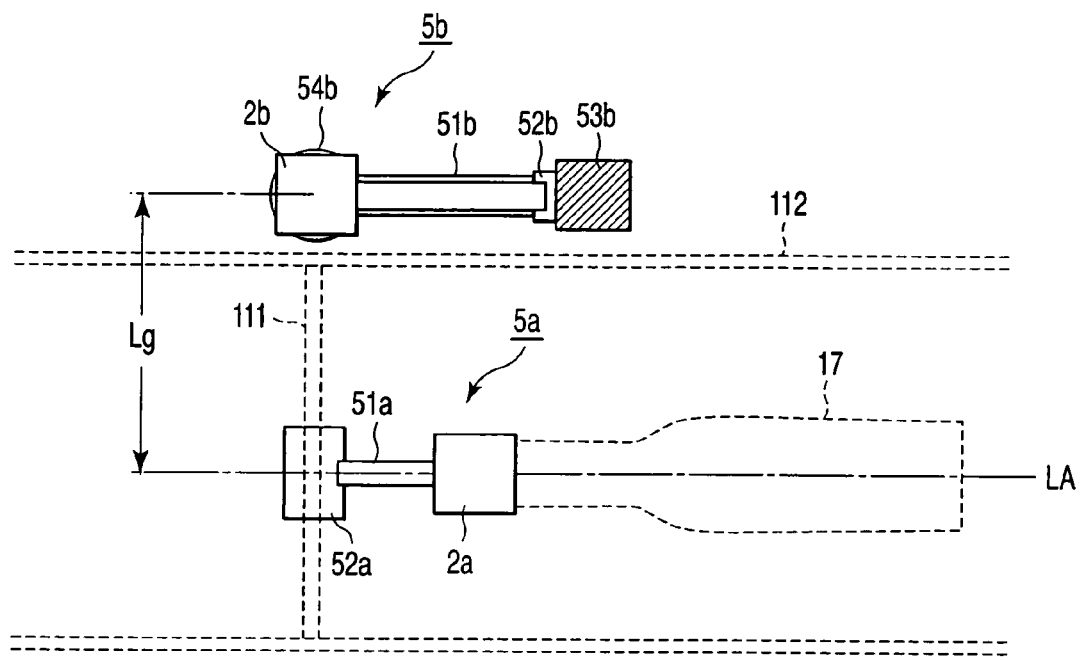
FIG. 7A is a view showing the retraction position of the floor type C-arm holding apparatus according to the modification of the embodiment.
Figure 7B:
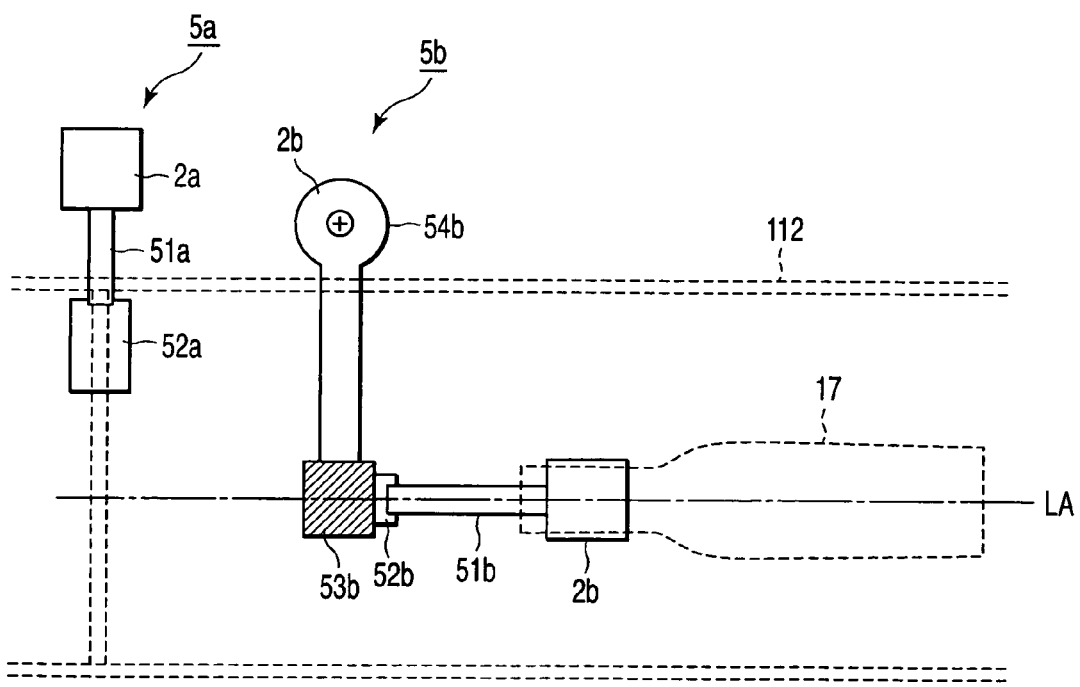
FIG. 7B is a view showing the retraction position of the ceiling-traveling C-arm holding apparatus according to the modification of the embodiment.

FIG. 7A shows the positional relationship between the ceiling-traveling C-arm holding apparatus 5a and the retracted floor type C-arm holding apparatus 5b in this modification. When a user instruction associated with the activation of the "floor type C-arm retraction mode" is input through the operation unit 9, the moving mechanism driving unit control unit 33 realizes the placement shown in FIG. 7A by controlling the respective units in response to the user instruction. Ceiling-traveling rails 112 are arranged on the ceiling of the examination room, and a slider base 111 is placed to be perpendicular to the ceiling-traveling rails. By moving an arm holder 52a of the ceiling-traveling C-arm holding apparatus 5a along the above ceiling-traveling rails 112 and the slider base 111, a C-arm 51a mounted on the arm holder 52a can be moved to a desired position. FIGS. 7A and 7B show the "head-first placement" of the ceiling-traveling C-arm holding apparatus 5a. In this case, since the floor type C-arm holding apparatus 5b is retracted to a side of the table top 17 at the distance Lg as in the case shown in FIG. 5, "head-first placement" by the ceiling-traveling C-arm holding apparatus 5a, which has been difficult to perform, is facilitated.

Note that the above floor type C-arm holding apparatus 5b is retracted on the basis of the selection information of the C-arm holding apparatus in the operation unit 9. A C-arm 51b is retracted outside the rotating range of the ceiling-traveling C-arm 51a. That is, the central axis of the ceiling-traveling C-arm 51a almost coincides with the longitudinal axis, and the C-arm 51b rotates so as to be almost parallel to the longitudinal axis. In addition, the C-arm 51b is retracted outside the rotating range of the ceiling-traveling C-arm 51a.

When the operator selects the ceiling-traveling C-arm holding apparatus 5a in selecting a C-arm holding apparatus by using the operation unit 9, the selection information is supplied to the moving mechanism driving unit control unit 33 of the moving mechanism driving unit 3 through the system control unit 10. Upon receiving this selection information, the moving mechanism driving unit control unit 33 supplies a driving control signal to the C-arm holding apparatus mechanism driving unit 31. The C-arm holding apparatus mechanism driving unit 31 supplies driving signals for pivoting a floor rotating arm 54b and a stand 53b to a floor rotating arm pivoting mechanism 514b and stand pivoting mechanism 513b (not shown) provided on the floor type C-arm holding apparatus 5b. By supplying these driving signals to the floor rotating arm pivoting mechanism 514b and the stand pivoting mechanism 513b, the floor type C-arm holding apparatus 5b shown in FIG. 7A is retracted.

FIG. 7B shows the positional relationship between the floor type C-arm holding apparatus 5b and the retracted ceiling-traveling C-arm holding apparatus 5a in this modification. When a user instruction associated with the activation of the "ceiling-traveling C-arm retraction mode" is input through the operation unit 9, the moving mechanism driving unit control unit 33 realizes the placement shown in FIG. 7B by controlling the respective units in response to the user instruction. The control unit 33 controls rotation of the C-arm 51b, movement of the slider base 111, movement of arm holder 52a, and rotation of the ceiling-traveling C-arm 51a in accordance with predetermined user instructions such that the central axis of the C-arm 51b which connects the first rotation axis Z1 to the second rotation axis Z2 is almost perpendicular to the longitudinal axis, and the ceiling-traveling C-arm 51a is retracted outside the rotating range of the C-arm 51b.

According to the above modification of this embodiment, when X-ray imaging is to be performed by using the ceiling-traveling C-arm holding apparatus of the X-ray diagnostic apparatus having the ceiling-traveling C-arm holding apparatus and the floor type C-arm holding apparatus, the stand of the floor type C-arm holding apparatus is pivotally mounted on one end of the floor rotating arm having the other end pivotally mounted on the floor surface. This makes it possible to retract the floor type C-arm holding apparatus to an area where it does not come into contact with the ceiling-traveling C-arm holding apparatus. Therefore, "head-first placement" using the ceiling-traveling C-arm holding apparatus, which has been difficult to perform, can be easily performed, and X-ray imaging can be performed at an optimal position or in an optimal direction in accordance with a purpose.

The embodiment of the present invention has been described above. However, the present invention is not limited to the above embodiment, and can be modified. For example, in the above embodiment, the rotation axis Z1 of the floor rotating arm 54 is spaced apart from the longitudinal central axis of the table top 17 by the predetermined distance Lg like the rotation axis Z2 of the stand 53. However, the floor rotating arm 54 moves near the floor surface 59, and hence does not interfere with the movement of the table top 17. For this reason, the floor rotating arm 54 can also be installed on the longitudinal central axis of the table top 17 within the longitudinal moving range of the table top 17.

The above embodiment has exemplified the case wherein the arm holder 52, stand 53, and floor rotating arm 54 each are designed to pivot. However, some or all of them may be designed to rotate.

The pivoting and rotating mechanisms for them are preferably operated remotely from the operation unit 9. However, adding manual operation by the operator makes it possible to facilitate fine adjustment of a moving position and retraction position.

In addition, according to the above description, when the C-arm holding apparatus 5 is to be retracted in FIG. 5, the imaging axis of the imaging system mounted on the C-arm 51 almost coincides with the rotation axis Z1 of the floor rotating arm 54. However, the present invention is not limited to this.

Note that the above embodiment has exemplified the X-ray detecting unit 2 having the flat panel detector 21. However, an X-ray detecting unit having an X-ray I.I. or the like may be used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus comprising:
    a floor rotating arm installed at one end on a floor surface so as to be rotatable around a first rotation axis;
    a C-arm mounted on the other end of the floor rotating arm so as to be rotatable around a second rotation axis;
    an X-ray tube mounted on one end of the C-arm;
    an X-ray detector mounted on the other end of the C-arm; and
    a bed including a table top provided to be movable along a longitudinal axis, the bed being placed such that the longitudinal axis is spaced apart from the first rotation axis by a predetermined distance,
    wherein a distance between the second rotation axis and an imaging axis is substantially equal to a distance between the first rotation axis and the second rotation axis, and the imaging axis is an axis which connects an X-ray focal point of the X-ray tube to a center of the X-ray detector,
    wherein a distance between the longitudinal axis and the first rotation axis is equal to a distance between the first rotation axis and the second rotation axis.

2. An apparatus according to claim 1, further comprising a control unit which controls rotation of the floor rotating arm in accordance with a predetermined user instruction such that a central axis of the floor rotating arm which connects the first rotation axis and the second rotation axis becomes substantially parallel to the longitudinal axis.

3. An apparatus according to claim 2, wherein the control unit controls rotation of the C-arm in accordance with the predetermined user instruction such that a central axis of the C-arm which connects the second rotation axis and the imaging axis becomes substantially perpendicular to the longitudinal axis.

4. An apparatus according to claim 2, wherein the control unit controls rotation of the C-arm in accordance with the predetermined user instruction such that the C-arm overlaps on the floor rotating arm.

5. An apparatus according to claim 1, further comprising a control unit which controls rotation of the floor rotating arm in accordance with a predetermined user instruction such that a central axis of the floor rotating arm which connects the first rotation axis and the second rotating axis becomes substantially perpendicular to the longitudinal axis.

6. An apparatus according to claim 5, wherein the control unit controls rotation of the C-arm in accordance with the predetermined user instruction such that a central axis of the C-arm which connects the second rotation axis and the imaging axis becomes substantially parallel to the longitudinal axis.

7. An apparatus according to claim 1, further comprising a pair of ceiling-traveling rails which are installed on a ceiling so as to be substantially parallel to the longitudinal direction, a slider base which is laid over the ceiling-traveling rails so as to freely travel, an arm holder which is provided on the slider base so as to freely travel, a ceiling-traveling C-arm which is mounted on the arm holder so as to be rotatable around a third rotation axis, another X-ray tube which is mounted on one end of the ceiling-traveling C-arm, and another X-ray detector which is mounted on the other end of the ceiling-traveling C-arm.

8. An apparatus according to claim 7, further comprising a control unit which controls rotation of the floor rotating arm, rotation of the C-arm, and rotation of the ceiling-traveling C-arm in accordance with predetermined user instructions such that a central axis of the ceiling-traveling C-arm substantially coincides with the longitudinal axis, and the C-arm is retracted outside a rotating range of the ceiling-traveling C-arm.

9. An apparatus according to claim 7, further comprising a control unit which controls rotation of the floor rotating arm, movement of the slider base, movement of the arm holder, and rotation of the ceiling-traveling C-arm in accordance with predetermined user instructions such that a central axis of the floor rotating arm which connects the first rotation axis and the second rotation axis becomes substantially perpendicular to the longitudinal axis, and the ceiling-traveling C-arm is retracted outside a rotating range of the floor rotating arm.

* * * * *